(12) United States Patent
Toi et al.

(10) Patent No.: US 7,374,720 B2
(45) Date of Patent: May 20, 2008

(54) CONTROL DEVICE FOR AUTOMATIC LIQUID HANDLING SYSTEM

(75) Inventors: Hiroatsu Toi, Hitachinaka (JP);
Hidetaka Osawa, Hitachinaka (JP);
Kenji Yamada, Hitachinaka (JP);
Tadashi Ohkawara, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 937 days.

(21) Appl. No.: 10/714,889

(22) Filed: Nov. 18, 2003

(65) Prior Publication Data
US 2004/0096365 A1 May 20, 2004

(30) Foreign Application Priority Data
Nov. 18, 2002 (JP) .......................... P2002-334431

(51) Int. Cl.
*B32B 5/02* (2006.01)
(52) U.S. Cl. .................... 422/67; 422/63; 422/64; 422/65; 422/66; 422/99; 422/100; 422/101; 436/180; 73/864.01; 222/267
(58) Field of Classification Search ............ 422/63–67, 422/99–101; 73/864.24, 864.01; 436/47, 436/180; 222/267
See application file for complete search history.

(56) References Cited

U.S. PATENT DOCUMENTS

| | | | |
|---|---|---|---|
| 4,586,546 A * | 5/1986 | Mezei et al. ............. | 141/2 |
| 5,443,791 A | 8/1995 | Cathcart et al. | |
| 5,985,214 A | 11/1999 | Stylli et al. | |
| 6,006,800 A * | 12/1999 | Nakano ................ | 141/130 |
| 6,207,031 B1 | 3/2001 | Adourian et al. | |

FOREIGN PATENT DOCUMENTS

| | | |
|---|---|---|
| DE | 42 10 963 | 10/1993 |
| EP | 0 114 686 | 10/1989 |
| JP | 5-232124 | 9/1993 |
| JP | 8-271528 | 10/1996 |
| JP | 2000-83650 | 3/2000 |
| WO | WO 02/49761 | 6/2002 |

OTHER PUBLICATIONS

English Translation of German Office Action dated Feb. 10, 2006.
German Office Action dated Feb. 10, 2006.

* cited by examiner

*Primary Examiner*—Jill Warden
*Assistant Examiner*—Jyoti Nagpaul (57) ABSTRACT

In reagent reaction experiments using microplates, the operator cannot just set dispensing tips in all the fixing holes of the dispensing tip container. It is necessary to carry out the time-consuming task of deciding in advance on a suitable arrangement of positions for the dispensing tips. It is also necessary for the operator to carry out the time-consuming task of determining in advance the quantity of reagent used and how the reagent is to be arranged. These problems are solved by providing a control device that includes a dispensing tip arrangement calculator and reagent quantity and arrangement calculator, and that can inform the operator of these results. The dispensing tip arrangement, the reagent quantity used, and the reagent arrangement is calculated from the information set in advance on specific reagent, the quantity of reagent dispensed into one well of the microplate, the range of wells in the microplate into which reagent is dispensed, and the direction of dispensing.

18 Claims, 8 Drawing Sheets

| PROCESS NUMBER | PROCESS NAME | PROCESS (CONDITIONS) | TIME REQUIRED (SECONDS) |
|---|---|---|---|
| 1 | DISPENSE | ROW 1 COLUMNS A TO E DISPENSE 144 μl REAGENT 1 IN ↑ DIRECTION | 62 |
| 2 | DISPENSE | FROM COLUMN A ROWS 2 TO 12 TO COLUMN E DISPENSE 100 μl REAGENT 2 IN → DIRECTION | 178 |
| 3 | DILUTE | PIPETTING 5 TIMES FROM ROW 1 COLUMNS A TO E TO ROW 8 DILUTING DISPENSE 50 μl IN ↑ DIRECTION | 117 |
| 4 | INCUBATE | AT 37°C FOR 10 MINUTES | 600 |
| 5 | DISPENSE | COLUMN A ROWS 1 TO 12 DISPENSE 100 μl REAGENT 3 IN → DIRECTION | 50 |
| 6 | DISPENSE | COLUMN B ROWS 1 TO 12 DISPENSE 100 μl REAGENT 4 IN → DIRECTION | 50 |
| 7 | DISPENSE | COLUMN C ROWS 1 TO 12 DISPENSE 100 μl REAGENT 5 IN → DIRECTION | 50 |
| 8 | DISPENSE | COLUMN D ROWS 1 TO 12 DISPENSE 100 μl REAGENT 6 IN → DIRECTION | 50 |
| 9 | DISPENSE | COLUMN E ROWS 1 TO 12 DISPENSE 100 μl REAGENT 7 IN → DIRECTION | 50 |
| 10 | INCUBATE → DISPENSE STOP SOLUTION | INCUBATE AT 37°C TIME TO DISPENSING STOP SOLUTION 30 MINUTES | 1800 |
| | | FROM COLUMN A ROWS 1 TO 12 TO COLUMN E DISPENSE 75 μl REAGENT 8 IN → DIRECTION | 220 |

CONTROL DEVICE FOR AUTOMATIC LIQUID HANDLING SYSTEM

BACKGROUND OF THE INVENTION

1. Field of the Invention

The present invention relates to the control device for an automatic liquid handling system that automatically calculates the distribution of dispensing tips for reagent or enzymes that are used in drug metabolic experiments.

2. Description of Related Art

In the development of new drugs, this type of experiment is frequently carried out, and each experiment is involved with a large amount of work. It is therefore essential to reduce mistakes caused by human error. To this end, there is a tendency that operations depending upon human operation shift to automatic operation.

As disclosed in Japanese Patent Application Publication No. 2000-83650, a conventional automatic test apparatus used in conducting metabolic experiments includes a three-dimensionally movable robot having a tip end on which a single dispensing probe is mounted. A vial rack with a group of four vials, a thermo-mixer, a cooling unit, and a specimen container are disposed in fixed locations and maintained in an upright position. The layout of these components can be arbitrarily changed.

The above-described apparatus is disadvantageous in that with a single dispensing probe, a number of experiments cannot be performed at high speed. Recently, microplates having wells formed in an n-by-m matrix are used instead of vials. The use of microplates reduces costs and the quantity of reagent. Recently, an automatic liquid handling system using the microplates have been proposed in which a large number of processings involved in a drug metabolic experiment can be performed at high speed. The handling system includes a robot with a dispensing head in which a plurality of dispensing tips is removably disposed in a row. When performing this type of experiment using such a handling system, the operator has to determine a suitable arrangement of the dispensing tips in a container.

At the same time, it is also necessary for the operator to calculate in advance the amount of reagent to be used in the experiment and how the reagent is to be arranged.

SUMMARY OF THE INVENTION

In view of the foregoing, it is an object of the invention to provide a control device for an automatic liquid handling system capable of determining the arrangement of dispensing tips in a container, calculating the amount of reagent to be used in an experiment, and determining how the reagent is to be arranged.

In accordance with the invention, there is provided an automatic liquid handling system that includes a dispensing tip container, a reagent container, a microplate formed with a plurality of wells, and a dispensing head. The dispensing tip container has a plurality of holding portions for holding dispensing tips. The reagent container holds one or more reagents. The dispensing head has attachment portions to which at least one dispensing tip is attached. When one or more dispensing tips are attached to the attachment portions, the dispensing head is capable of performing sucking and expelling operations. Specifically, the dispensing head can suck the reagent into the dispensing tips from the reagent container, expel the reagent out from the dispensing tips, and dispense or drip the reagent into the wells of the microplate. Also, the dispensing head can suck the liquid in the specified wells of the microplate and dispense the sucked liquid into another specified wells. Moving means is also provided for moving the dispensing head. The liquid handling system also includes a control device that controls the sucking and expelling operations performed by the dispensing head and also controls the moving means to control movements of the dispensing head. The control device has input means for inputting one or more processes to be executed by the dispensing head. A dispensing tip arrangement calculating means is also provided for calculating an arrangement of the dispensing tips in the dispensing tip container based on information contained in the one or more processes input into the control device.

Reagent volume calculating means is further provided in addition to the dispensing tip arrangement calculating means or the reagent volume calculating means may be provided independently of the dispensing tip arrangement calculating means. The reagent volume calculating means calculates a volume of the reagent to be dispensed into the wells of the microplate based on information contained in the one or more processes input into the control device.

Further, reagent arrangement calculating means is provided in addition to the dispensing tip arrangement calculating means and the reagent volume calculating means. However, the reagent arrangement calculating means may be provided independently of the dispensing tip arrangement calculating means and the reagent volume calculating means. The reagent arrangement calculating means calculates an arrangement of the reagent in the reagent container based on information contained in the one or more processes input into the control device.

DETAILED DESCRIPTION OF THE PREFERRED EMBODIMENTS

Figure 1:
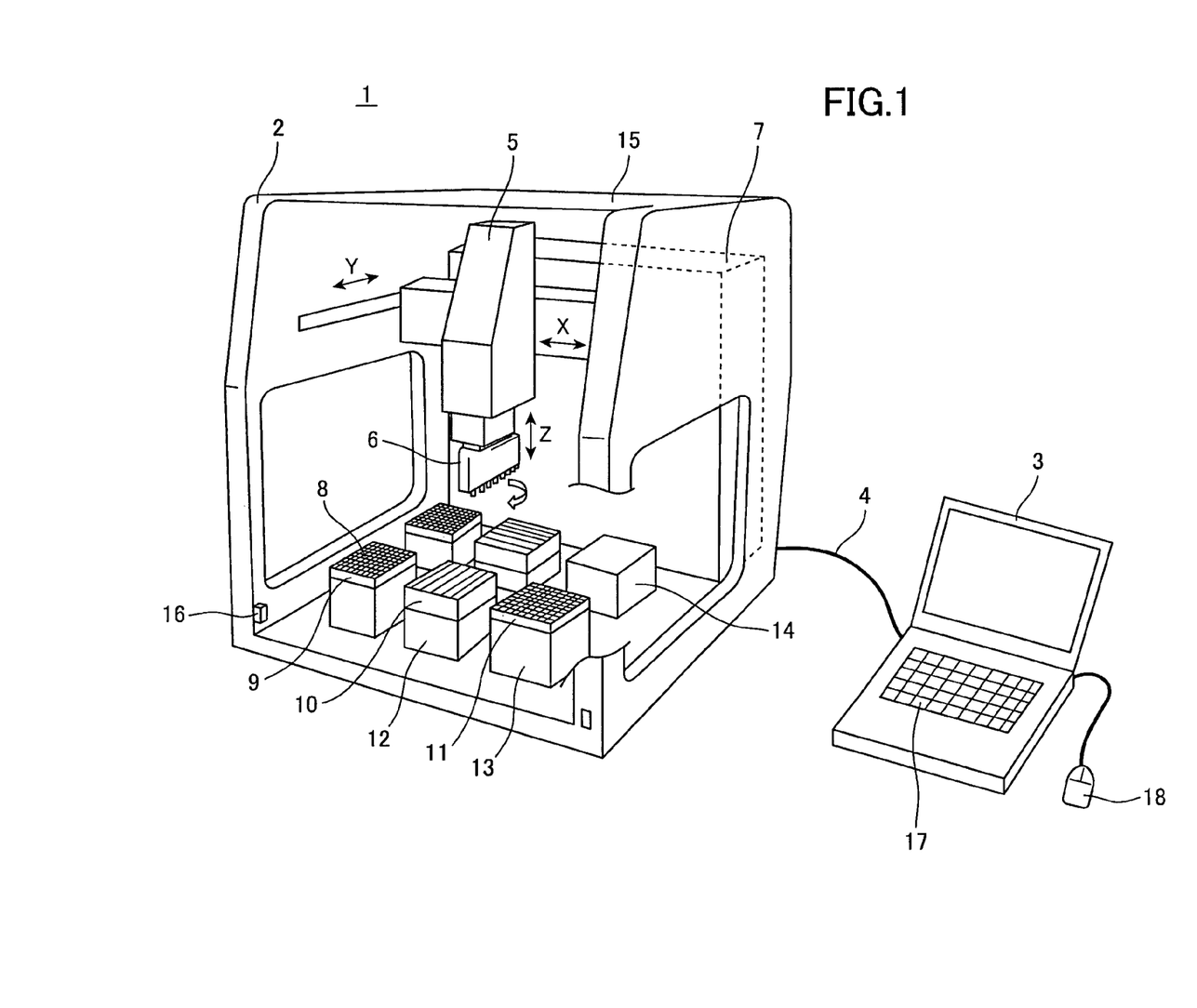
FIG. 1 is a perspective view of an automatic liquid handling system according to an embodiment of the present invention.

A preferred embodiment of the present invention will be described with reference to the drawings. FIG. 1 shows an automatic liquid handling system 1 according to a preferred embodiment of the present invention. The automatic liquid handling system 1 includes a main body 2 and a control device 3 connected together with a communication cable 4 such as a LAN (Local Area Network) cable. A general-purpose personal computer is used as the control device 3. The main body 2 of the automatic liquid handling system 1 includes a robot 5 capable of moving and stopping in 3D space, a dispensing head 6 provided at a tip end of the robot 5, and a driving circuit 7 for driving the main body 2 based upon conditions input into the control device 3.

The robot 5 has three orthogonal axes, X, Y, and Z, and is capable of being moved by stepper motors (not shown) to a predetermined position. Servo-motors can be used instead of the stepper motors. A plurality of dispensing tips 8 aligned at an equi-pitch can be removably attached to the dispensing head 6. The dispensing head 6 to which a dispensing tip a is attached can suck or expel liquid. For example, the dispensing head 6 described above can hold twelve syringes (not shown in the drawings) which are driven by one stepper motor. The spacing between syringes is 9 mm pitch, the same as the spacing between wells of a microplate 11. When a dispensing tip 8 is attached to the dispensing head 6, liquid can be sucked in or expelled out by driving the syringe.

Arranged beneath the dispensing head 6 of the robot 5 are a dispensing tip container 9, reagent containers 10, the microplate 11, and a disposal container 14. The dispensing tip container 9 has dispensing tip holding portions arranged at a pitch same as the well pitch of the microplate 11, that is, 9 mm pitch. The reagent container 10 holds reagent that is used in an experiment. The microplate 11 holds a specimen subject to the experiment. The disposal container 14 holds used dispensing tips 8. A plurality of wells is formed in the microplate 11 in an n-by-m matrix arrangement. For example, an 8-by-12 arrangement would have 96 wells. Also, the dispensing head 6 is capable of swiveling through 90 degrees, so that it is capable of dispensing to the microplate 11 in the two orthogonal directions.

A cover 15 is provided to the ceiling part and the side faces of the main body 2 of the automatic liquid handling system 1. Also, a door (not shown in the drawings) is provided to the front of the main body 2 of the automatic liquid handling system 1. The door is opened when preparing reagent or test specimens, and during execution of the experiment the door is closed and the automatic liquid handling system is operated. For the sake of safety of the operators, a reed switch 16 is provided to detect whether the door is open or closed. When the door is open, the contacts of the reed switch are rendered open, causing the electrical power lines to the motors to interrupt and thus the robot to stop.

Figure 2:
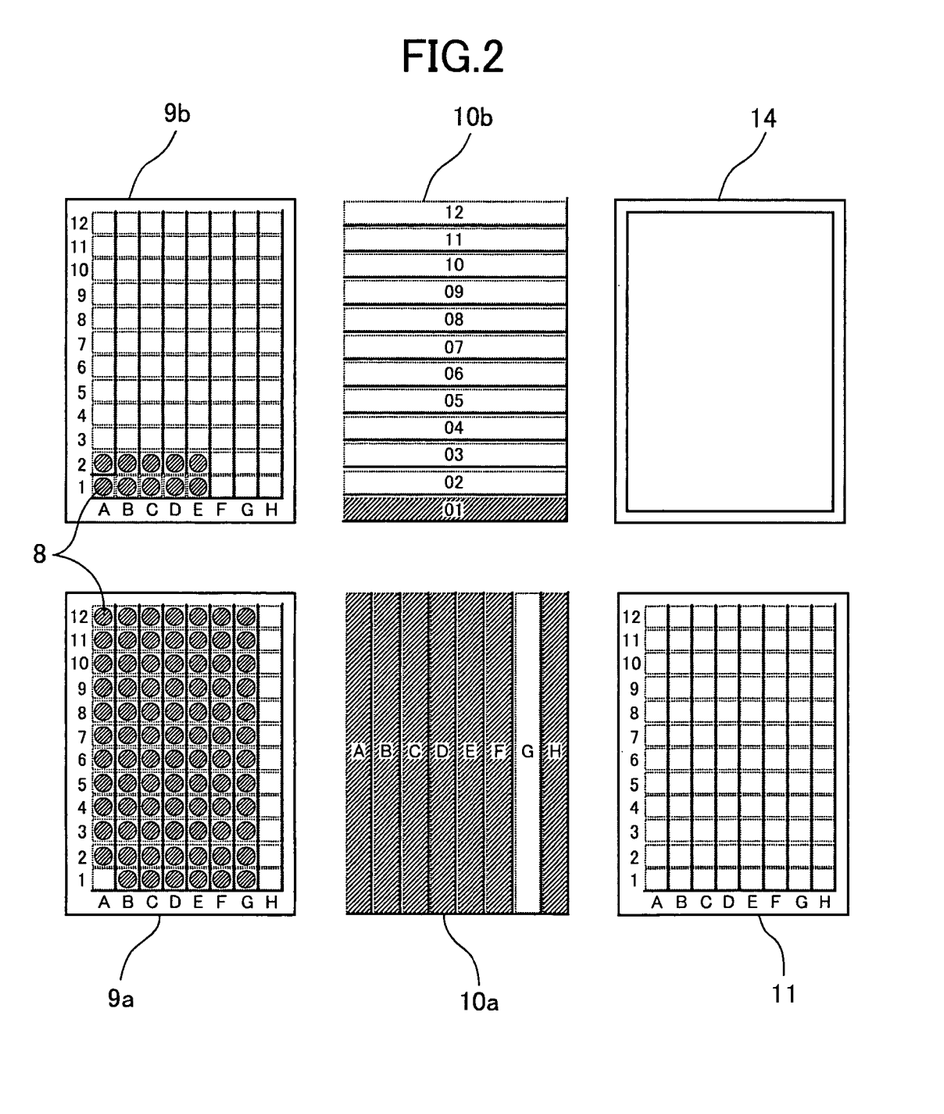
FIG. 2 is an explanatory diagram illustrating an arrangement of dispensing tip container, reagent container, microplate, and disposal container.

FIG. 2 shows an arrangement of each of the containers as viewed from above. In the arrangement shown in FIG. 2, dispensing tip containers 9a and 9b are disposed at the left side for holding the dispensing tips 8 arranged in an array. Reagent containers 10a and 10b are disposed at the center, and the microplate 11 and the disposal container 14 are disposed at the right side. The area for holding reagent in the reagent container 10a is divided into columns "A" to "H". Also the area for holding reagent in the reagent container 10b is divided into rows "1" to "12". Different reagents can be dispensed into each row or column of reagent containers 10a and 10b. When the dispensing head 6 is in such an orientation that the lengthwise direction of the head 6 is in coincidence with the direction in which the column extends, the dispensing tip container 9a and reagent container 10a are used. When the dispensing head 6 is swiveled 90 degrees and the lengthwise direction thereof is in coincidence with the direction in which the row extends, then the dispensing tip container 9b and reagent container 10b are used. The disposal container 14 is sufficiently large for disposing of the used dispensing tips regardless of whether the dispensing head 6 is oriented in the direction of column or row. The arrangement shown in FIG. 2 is only an example, and the arrangement of containers can be freely changed to suit the requirements of the experiment. However, it is necessary to input and save information regarding the arrangement of containers to the control device in advance.

When carrying out reagent reaction experiments, the reagent is normally refrigerated. In this embodiment, a cooling device 12 is disposed below the reagent containers 10a and 10b, as shown in FIG. 1, to maintain the reagent at, for example, 4° C. Also, in order to shake the microplate 11 after reagent is dispensed into the microplate 11, the microplate 11 is placed on a shaker 13 and is shook thereby while maintaining a fixed temperature. This operation is referred to as incubating.

The control device 3 controls the robot 5 to bring the dispensing head 6 to the desired position, and controls the dispensing head 6 to execute liquid sucking in or expelling operations. Also, the process (protocol) of a reagent reaction experiment, such as that shown in FIG. 3, can be input to the control device 3. For inputting the process to the control device 3, a keyboard 17 or a mouse 18 is used.

Figure 3:
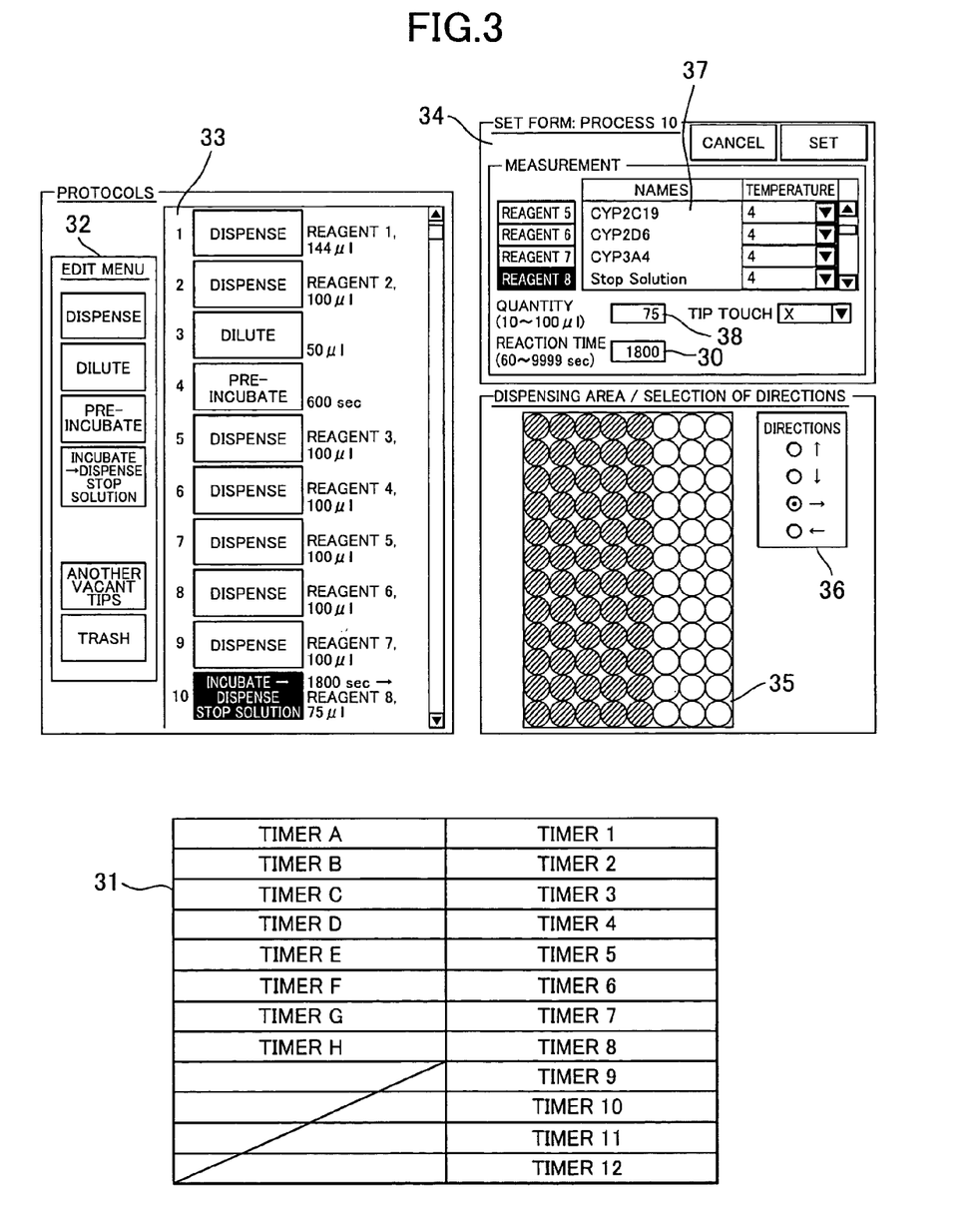
FIG. 3 shows an example of the screen for creating the process and timers according to an embodiment of the present invention.

FIG. 3 shows an example of an input screen for inputting the process. When inputting the process, one process to be executed is selected from an edit menu 32, and the process is transferred to a process column 33. For example, if dispense is selected from the edit menu 32 and transferred to the process column 33, an information input screen 34 appears for inputting all the information needed for the dispense operation. With the information input screen 34, various kinds of information can be input including reagent 37 to be selected, the dispense quantity 38, the range of dispense destination wells 35, and dispense direction 36, For example, the symbol→means to carry out dispense operations in the direction from column "A" toward column "H" in the microplate 11. Also, the symbol ↑ means to carry out dispense operations in the direction from row "1" toward row "12" of the microplate 11.

The right side of FIG. 3 shows an information input screen 34 for a process from incubate to dispensing stop solution. The information input screen 34 includes a time setting portion 30 for setting a period of time before the stop solution is dispensed (hereinafter referred to as "predetermined period of time"). The range of wells in the microplate 11 into which stop solution is to be dispensed can be specified on an individual basis or on a row or a column basis. Furthermore, the control device 3 includes timers 31 for measuring a period of time from immediately after reagent is dispensed into each row or column of the microplate 11. When the control device 3 is executing a process, the control device 3 compares the period of time measured by the timer 31 with the predetermined period of time. The dispense reaction stop solution operation will not be executed before the measured period of time has reached the set period of time.

Also, the control device 3 includes a dispensing tip arrangement calculator 70 and a reagent volume/arrangement calculator 80. The dispensing tip arrangement calculator 70 determines the arrangement of dispensing tips 8 in the dispensing tip containers 9 based on input information regarding the dispensing wells in the microplate 11 and also dispensing direction. The arrangement of dispensing tips 8 thus determined is displayed for the operator's convenience. The reagent volume/arrangement calculator 80 calculates the quantity of reagent 37 to be used and determines the arrangement of reagent 37 in the reagent containers 10a and 10b based on the reagent 37 to be used, the dispense volume 38 per well of the microplate 11, the number of wells 35 in which the reagent 37 is to be dispensed, and information regarding the dispense direction 36. The calculated quantity of reagent 37 and the arrangement of reagent 37 thus determined are displayed for the operator's convenience and are also stored in a memory device (not shown). The use of the stored information can eliminate re-calculation for the same conditions, thereby reducing the time necessary for calculation.

Furthermore, the control device 3 includes a self-determination function 40. The self-determination function 40 can simulate the time to execute the processes input in advance for a reagent reaction experiment, and determine whether the automatic liquid handling system 1 can execute the operations in the time specified at the time setting portion 30, and inform the operator of the result.

Figure 6:
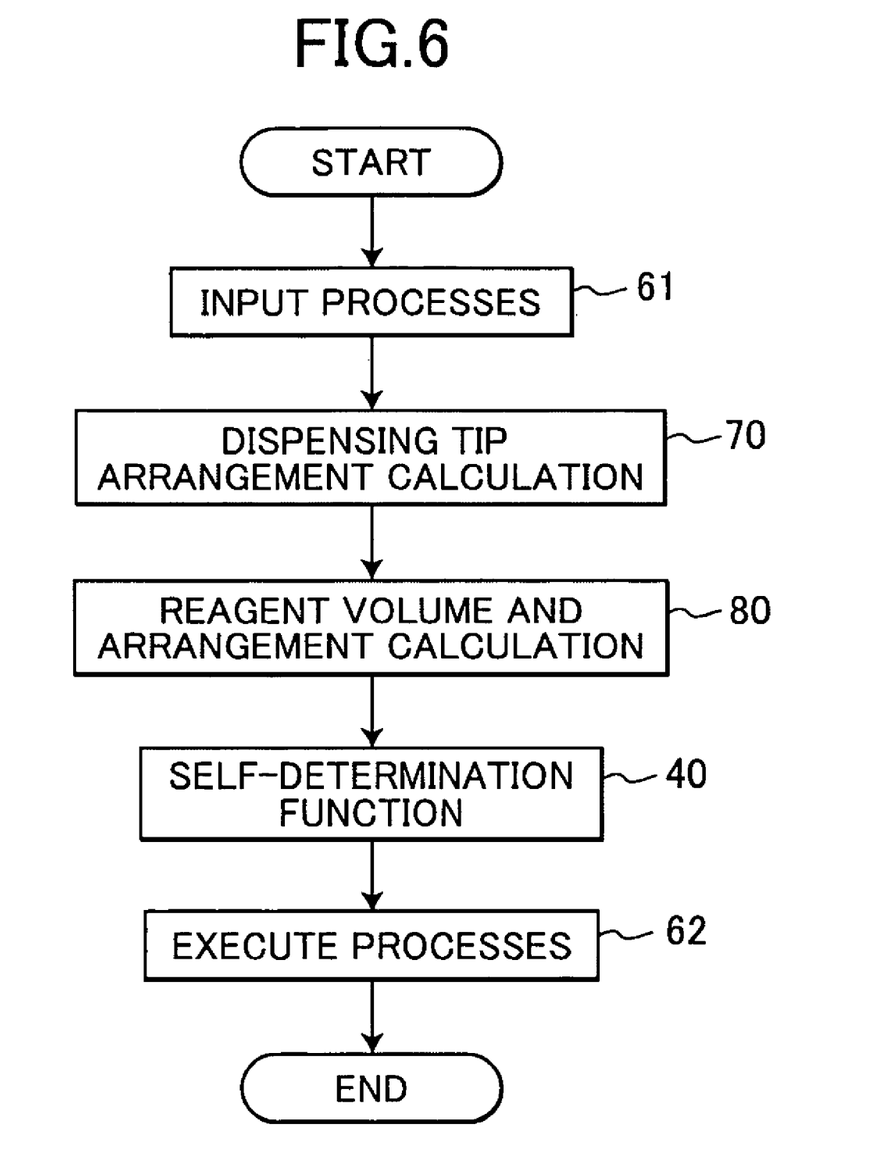
FIG. 6 is a flowchart showing the sequence of operations from the input of the process to execution of the process.
Figure 8:
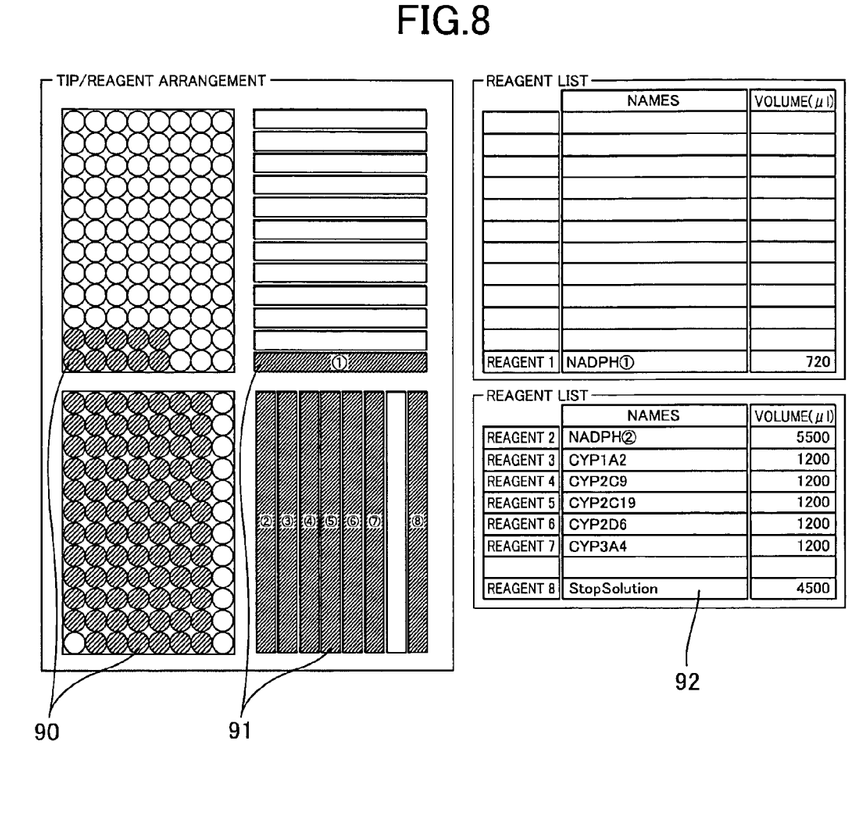
FIG. 8 is an explanatory diagram showing an arrangement of dispensing tips and reagent and an indication of the quantity of reagent according to an embodiment of the present invention.

Next, the sequence in time for executing each of the functions of the control device 3 described above will be described referring to the flowchart shown in FIG. 6. At step 61, the operator inputs the processes that are to be executed. Next, the dispensing tip arrangement calculator 70 and the reagent volume/arrangement calculator 80 are executed. Then the self-determination function 40 determines whether the automatic liquid handling system 1 can execute the processes within the time specified at the time setting portion 30 or not. If the automatic liquid handling system 1 is not capable of executing the processes within the specified time, then an alarm is activated, and the operator is instructed to input the processes again. If the automatic liquid handling system 1 is capable of executing the processes within the specified time, then the dispensing tip and reagent arrangements are displayed, together with the reagent quantities, as shown in FIG. 8. The operator sets up each of these items in accordance with the display on the screen. When these preparations are completed, the operator causes the processes to be executed (step 62).

Figure 7:
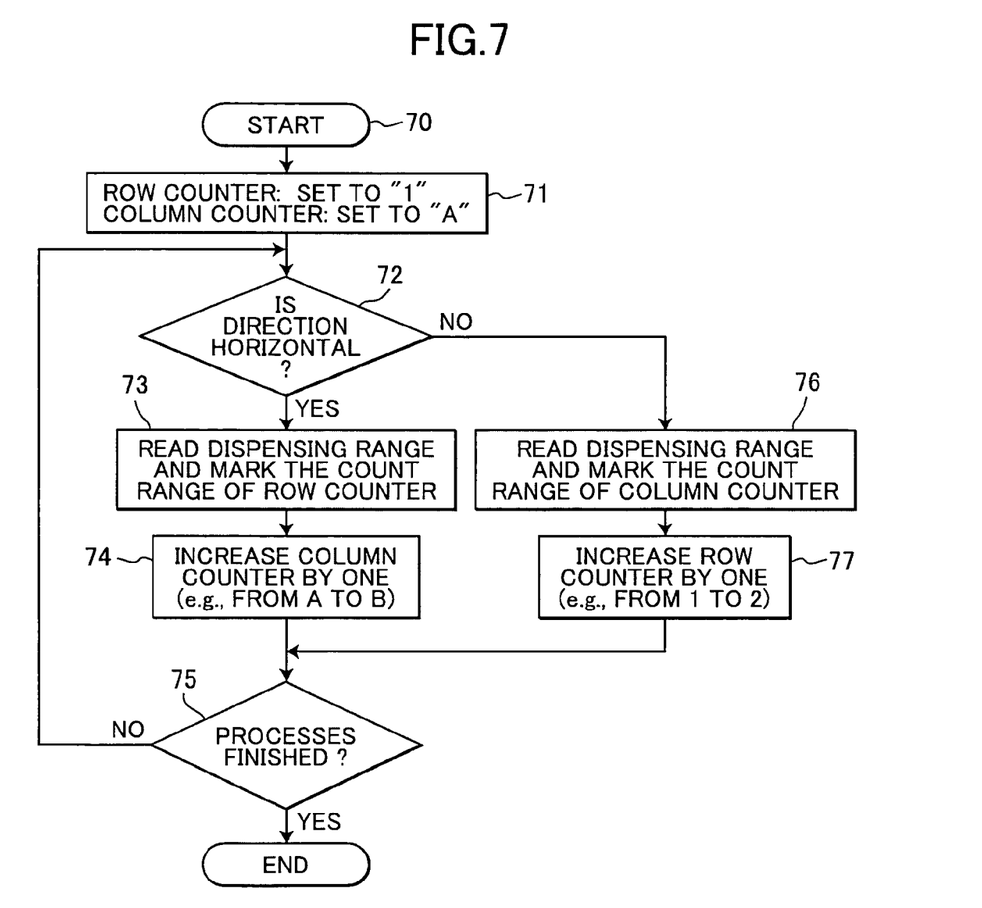
FIG. 7 is a flowchart showing the sequence of operations to be executed for determining the dispensing tip arrangement according to an embodiment of the present invention.

Next, referring to the flowchart in FIG. 7 and the process table shown in FIG. 9, description will be made with respect to the dispensing tip arrangement calculating function 70. It should be noted that in the dispensing tip container 9a, the dispensing tips 8 are firstly arranged on column "A" and this columnar directional tip arrangement is performed one after another in the direction from column "A" toward column "H". This direction will be referred to as "horizontal direction" for the purpose of description. Also, in dispensing tip container 9b, the dispensing tips 8 are firstly arranged on row "1" and this row directional tip arrangement is performed one after another in the direction from row "1" toward row "12". This direction will be referred to as "vertical direction" for the purpose of description.

In the initialization step 71, the row counter is set to "1" and the column counter to "A". In step 72, decision is made as to whether or not the dispensing tips 8 are to be arranged in the horizontal direction. Referring to the process number 1 shown in the table of FIG. 9, the dispense direction is indicated by an upwardly directed arrow meaning that dispensing is performed in the vertical direction. Therefore, "NO" is the decision made in step 72 and the process proceeds to step 76 where dispensing range on wells of the microplate 11 is read from the process table shown in FIG. 9. The process table indicates that the dispensing tips 8 to be arranged on row "1" are in a range from column "A" to column "E". Accordingly, the column counter is marked with "A" to "E" as a count range.

Next, in step 77, the row counter is incremented by 1 to become "2". Then, in step 75, it is determined whether or not the scheduled processes are finished. If further processes remain, then the procedure returns to step 72 to determine what the next process is. The dispense direction in the next process, process number 2, is indicated by a leftwardly directed arrow in the process table shown in FIG. 9, so the procedure proceeds to step 73. The process to be performed in process number 2 is dispensing in the microplate wells that are enclosed by a rectangle whose diagonal line is defined by points (A,2) and (E,12). Therefore, the range of rows "2" to "12" in column "A" of the dispensing tip container 9a are marked. Next, in step 74 the column counter is incremented by one to change from "A" to "B". Then, in step 75 the procedure checks whether the processes are all complete, and if further processes remain, the procedure checks for details of process number 3. Then, the procedure as described above is executed, and the dispensing tips used for process number 3 is arranged in the dispensing tip container 9b in positions of row "2" from columns "A" to "E". In this manner, one column or row is processed at a time until process number 10 is reached. The screen displays the arrangement of dispensing tips 8 as shown in FIG. 8.

The marking of the dispensing tip arrangement 90 can use different colors for the dispensing tips 8 needed in each process. If this type of display is adopted, then the likelihood of a mistake in the arrangement of dispensing tips 8 is further reduced. Also, the method of displaying each process can use either symbols, numbers letters, or the like.

Next, the reagent volume and reagent arrangement calculating function 80 for calculating the volume of reagent used and the arrangement of reagent will be described. The quantity of reagent used is the product of the specified dispense volume and the specified number of wells. For example, in process number 1, the dispense volume is 144 μl (micro litter) and the number of wells is 5, and the product of these is 720 μl. In process number 2, the dispense volume is 100 μl and the number of cells is 11×5, and the product of these is 5500 μl. If the same reagent is used in different processes, then their volumes can be summed. Next, to determine the reagent layout, a procedure similar to that shown in FIG. 7 is executed. Specifically, the procedure determines whether to set the reagent in reagent container 10a or reagent container 10b depending upon the dispense direction, and the arrangement is determined in order, according to the specified reagent. Particularly, in order to avoid contamination of other reagents by the stop solution, the operator can specially arrange the stop solution to be separated from the other reagents. In this manner, the volume of reagent is calculated and the arrangement of reagent is determined. FIG. 8 shows the display of the results, the arrangement of reagents 1 to 8 is displayed as denoted by reference numeral 91, and the volume of reagent used is displayed as denoted by reference numeral 92. Referring to the reagent volumes in 92, the operator can dispense slightly more reagent to account for dead volume.

Also, in the display in 91, the reagent used in each process can be shown in separate colors. If this type of display is adopted, then the likelihood of a mistake in the arrangement of reagent is further reduced. Also, the method of displaying each process can use either symbols, numbers, letters, or the like. Also, if the same reagent is used several times, then the positions displayed can be split.

Next, the self-determination function will be described. As described above, an operator prepares a process table of the processes that are to be executed, such as the table shown in FIG. 9. The processes are input to the control device 3.

Figure 5:
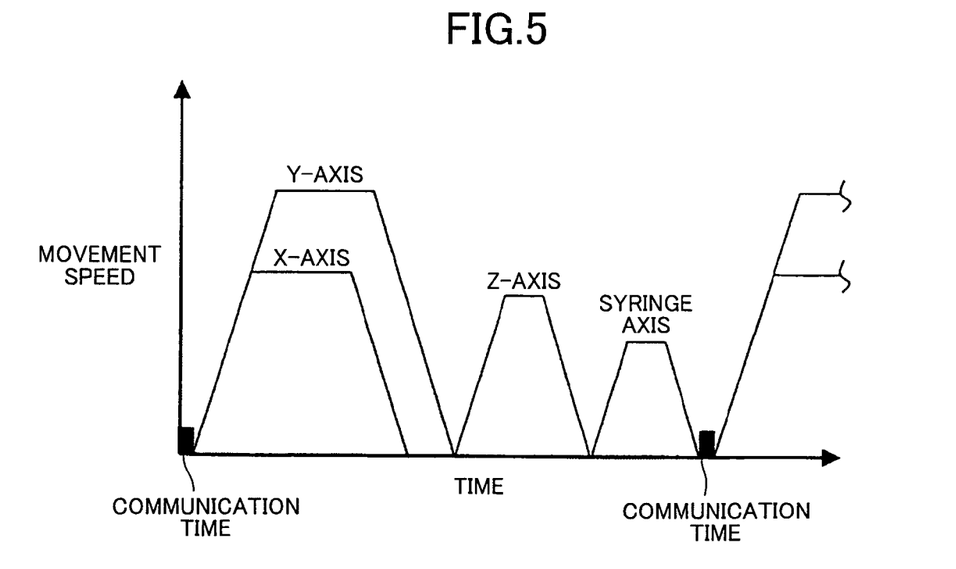
FIG. 5 is a graphical representation showing movement of a robot.

The control device 3 has a function for calculating the actual time required from the processes input. For example, the robot 5 is moved in accordance with a trapezoid acceleration/deceleration pulse train, so the movement and dispense time can be calculated from the predetermined acceleration or deceleration, maximum speed, traveling distance, etc. Naturally, when several axes are moving simultaneously, it is the axis with the longest movement time that is selected. In the example shown in FIG. 5, the robot 5 is firstly moved along the X- and Y-axes simultaneously at the same speed. When positioning of the Y-axis is determined, the robot 5 is moved in the direction of Z-axis. That is, the robot 5 is moved to a predetermined height. Then, the syringe axis is driven in order to suck in or expel reagent into or out of the dispensing tips 8. The times for these movements are calculated. Because each movement is controlled by the control device 3, data transmission time needs to be taken into consideration to obtain the total time required for executing all the operations. It is possible to calculate the data transmission time from the amount of data and the transmission speed. It is therefore possible to simulate the time required for each process by summing the time required to execute each operation in the process and the data transmission time. For example, in the case of process number 1 in FIG. 9, the time required to attach the dispensing tips, suck in the reagent 1 and dispense the reagent in the microplate 11, dispose the dispensing tips 8 in the disposal container 14, and the time required to transmit the commands for each of these operations can be calculated and summed. The result of summing these times is the time required to execute process number 1. In this way, as shown in the "Time Required" column of FIG. 9, the control device 3 can calculate the time required to execute each process.

Figure 4:
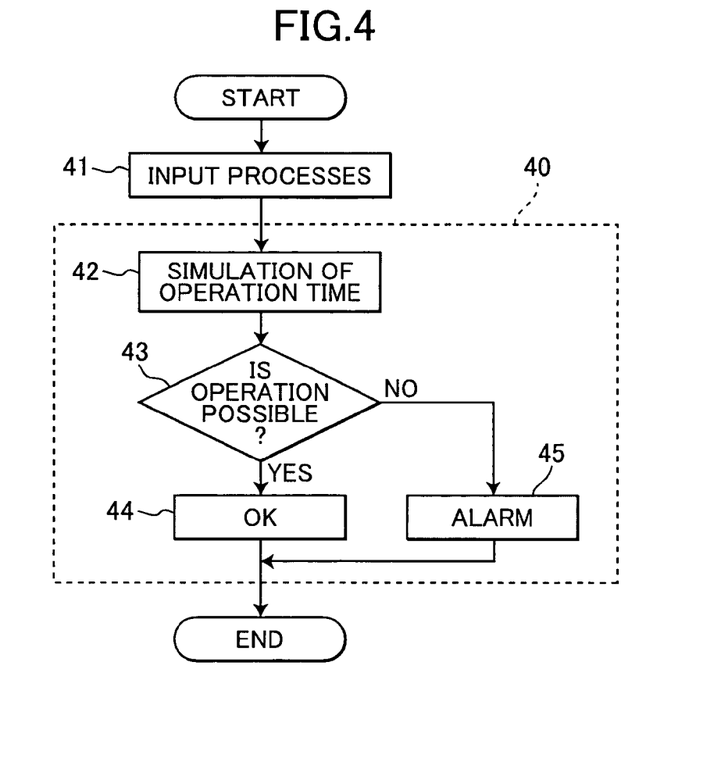
FIG. 4 is a flowchart showing the self-determination function of an embodiment of the present invention.

The self-determination function 40 of the control device 3 determines whether the calculated operation time is in accordance with the required time input at the time setting 30, and informs the operator. Specifically, as shown in the flowchart in FIG. 4, the self-determination function 40 is executed after inputting the processes (step 41). First, the operation time simulation is executed (step 42). Then, the procedure determines whether the processes can be completed within the time input at the time setting 30 (step 43). If it is possible to execute the processes within the time input at the time setting 30, then the message "OK" is output to the screen (step 44). If it is not possible, then "Alarm" is displayed (step 45) to alert the operator that it is not possible to execute the processes within the time input at the time setting 30.

During the simulation, in accordance with the progress of the experiment, it is possible to display on the screen the status of use of the dispensing tips 8 displayed in the arrangement 90, the status of use of reagent displayed in 91, the status of dispensing in the microplate 11, using for example colors, symbols, or letters. In this way, the operator can accurately grasp the status of the simulation. This kind of display can be carried out not only during the simulation, but also during actual execution of the processes.

Figure 9:
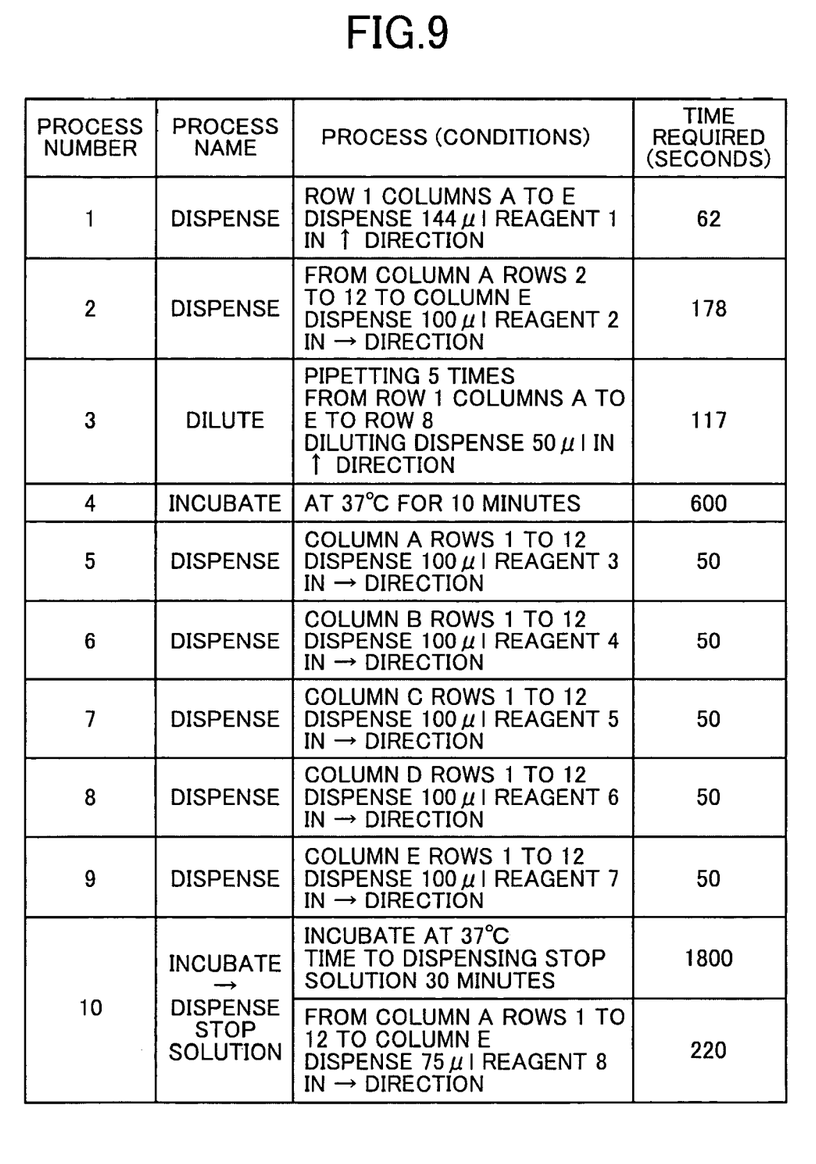
FIG. 9 shows an example of a process table for a metabolic experiment.

The following is an explanation of the actual operation, using the processes shown in FIG. 9 as an example. Firstly, the operator adds by hand 6 μl of the test specimen to wells A to E of row 1 of the microplate 11 in advance. The microplate 11 is placed on the shaker 13, and the door is closed. Then, the operator starts the processes input to the control device 3.

In process number 1, the automatic liquid handling system 1 attaches the five dispensing tips 8 set in the dispensing tip container 9b in columns "A" to "E" of row "1". Next, 144 μl of reagent in the reagent container 10b is sucked in, and dispensed in wells in columns "A" to "E" of row "1" of the microplate 11 placed on the shaker 13. The amplitude of shaking of the shaker 13 is about +/−1 mm, which is sufficiently small compared with the diameter of the wells, 8 mm. Therefore, even during incubation operations, dispensing operations can be carried out. After dispensing operations are completed, the dispensing tips 8 are disposed of in the disposal container 14 in order to avoid contamination.

In process number 2, the automatic liquid handling system 1 attaches the eleven dispensing tips 8 set in column "A", rows "2" to "12" of dispensing tip container 9a. Before this operation, the dispensing head 6 is rotated through 90 degrees. Then, 100 μl of reagent 2 in "A" of reagent container 10a is sucked in, and dispensed in wells "2" to "12" of column "A" of the microplate 11 placed on top of the shaker 13. Then, 100 μl of reagent 2 in "A" of reagent container 10a is again sucked in, and dispensed to wells "2" to "12" of column "B". This operation is repeated until the operation in column "E" is executed, and the dispensing tips 8 are disposed of to the disposal container 14.

The rotation of the dispensing head can be accomplished using, for example, a stepper motor or a solenoid or other type of actuator. Alternatively, a disk can be provided on the dispensing head, and an abutment member provided on the main body 2 of the automatic liquid handling system 1, so that the abutment member is capable of contacting the disk on the dispensing head 6. While the disk is contacting the abutment member, the dispensing head 6 is moved in the X or the Y-axis, causing the dispensing head 6 to rotate. The axis of rotation of the dispensing head 6 corresponds to the center of the dispensing head 6.

For the dilution operation in process number 3, firstly the dispensing head is rotated and the dispensing tips 8 set in row "2", columns "A" to "E" of dispensing tip container 9b are attached to the dispensing head 6. The dispensing head 6 moves to row "1" of the microplate 11 on top of the shaker 13, and dips the dispensing tips 8 into the liquid in wells "A" to "E" of row "1". An agitation operation consisting of sucking in and expelling out the liquid is repeated five times. Then, 50 μl of liquid is sucked in, and 50 μl is dispensed into the neighboring wells "A" to "E" of row "2". This liquid is sucked in and expelled out five times. In the same way, 50 μl from row "2" is dispensed into row "3", then agitated and diluted. This type of operation is repeated until row "8". The dispensing tips 8 are disposed of in the disposal container 14 together with the 50 μl of liquid sucked in from row "8". In this process, diluted test specimen is generated in row "1" to "8" of the microplate 11.

In process number 4, an incubation operation is carried out by shaking the microplate 11 for 10 minutes at a fixed temperature, for example 37° C. The control device 3 executes the following process after the 10 minutes incubation time is complete.

Process numbers 5 to 9 are processes for dispensing reagent into the wells of columns "A" to "E" of microplate 11. The following is an explanation of how timers A to E provided for each column of microplate 11 measure the time from dispensing reagent.

In process number 5, the dispensing head rotates through 90 degrees to be oriented in the direction of column A, and attaches the dispensing tips 8 set in rows "1" to "12" of column B of the dispensing tip container 9a to the dispensing head 6. Next, 100 μl of reagent 3 contained in B of reagent container 10a is sucked in, and dispensed to wells "1" to "12" of column "A" of the microplate 11 on top of the shaker 13. Immediately after this, the control device 3 causes the timer A to clear to 0 and start counting up. Timer A counts up in units of one millisecond, for example. After dispensing, the twelve dispensing tips 8 are disposed of in the disposal container 14.

In process number 6, similar to process number 5, 100 μl of reagent 4 contained in "C" of reagent container 10*a* is sucked in, and dispensed to wells "1" to "12" of column B of the microplate 11. Immediately after this, the control device 3 causes the timer B to clear to 0 and start counting up.

Thereafter, similar processes are executed until process number 9, with reagents 5 to 7 being dispensed to columns "C" to "E" of the microplate 11, and timer C, timer D, and timer E started.

The time required for each dispensing operation is 50 seconds. Therefore, timer B is 50 seconds later than timer A, and timer C is 50 seconds later than timer B, and similarly for timers D and E.

In process number 10, the microplate 11 in which reagent has been dispensed is incubated for 30 minutes at 37° C., following which 75 μl of stop solution is dispensed into columns "A" to "E" of the microplate 11. Firstly, dispensing tips 8 from column "G" of dispensing tip container 9*a* are attached to the dispensing head 6. Then, 75 μl of reagent, which is reaction stop solution, in column "H" of reagent container 10*a* is sucked in. The incubation operation is executed while comparing the desired reaction time input at the time setting 30, in other words 30 minutes or 1,800 seconds, with the time on the timer A. When the time on timer A reaches the 1,800 seconds, reagent 8 is dispensed into column "A" of the microplate 11. After dispensing, reagent is again sucked in, and the dispensing head waits at column B of the microplate 11. When timer B reaches 1,800 seconds, reagent B is dispensed into column B. Thereafter, similar operations are executed until reagent is dispensed into column "E" and reagent reactions are stopped in each of columns "A" to "E". The control device 3 measures the time on timers A to E, in other words, the time from immediately after reagent is dispensed until the time when stop solution is dispensed. This time can be displayed on the screen, or recorded to a memory medium or printer not shown on the drawings. The position where the dispensing head waits for the reaction time to be complete is not necessarily above the wells, but a suitable position would be where even if drops of the stop solution sucked into the dispensing tips 8 fell from the dispensing tips 8, they would cause no obstruction to the experiment. Also, stop solution for which temperature control is critical, and whose temperature would change to the ambient temperature if left standing in the dispensing tips 8, can be sucked from column "H" of the reagent container 10*a* just before the end of the reaction time.

The subsequent operations consist of the operator removing the microplate 11, and measuring the fluorescence intensity of the reaction products using a fluorescent plate reader (not shown).

The time setting 30 described above is provided in the "Incubate→Dispense stop solution" information input screen 34. However, information input screen 34 for processes dispensing reagent for which time control is important can also be provided. A timer 31 is provided for measuring the time from dispensing the reaction start reagent for every column of the microplate 11, so it can be easily understood that an operation similar to the one described above can be performed.

In the processes taken as an example and described above, the time until dispensing the stop solution was 30 minutes. However, if this time were, for example, three minutes, then the time would finish during the time between executing process number 5 and process number 9. In this case, the self-determining function 40 described above would simulate the actual process time for the processes created, and confirm whether the operations were possible or not. In other words, the self-determination function would determine whether, for example, during the time from start of process number 5 to the time of dispensing the stop solution, there was sufficient time to execute another process.

Also, in the process examples described above, the reaction time for the different reagents was set to the same duration. However, it is also possible to carry out experiments where the same reagent is added to the test specimen, and different times are provided for each column. In this case, after dispensing to the range of wells for the reagent, the time set at "Incubate→Dispense Stop solution" will be different for each column. In this kind of experiment, even if a fault should occur in the equipment during execution of a process or for some reason it becomes necessary to stop the equipment, then because the timer 31 will have measured the actual time from immediately after dispensing the reagent until the stop solution was dispensed, use can be made of the test results for the experiment.

In the embodiment of the present invention described above, an example was given where dispensing tips 8 were disposed of. However, fixed tips that are cleaned can also be used. Also, a microplate 11 with 96 wells was used as an example in the description. However, the present invention can also be easily applied to a dispensing head 6 for microplates 11 for smaller quantities with 384 wells or 1,536 wells.

The control device of the automatic liquid handling system can calculate or determine the arrangement of the dispensing tips in the dispensing tip container using the information on the range of wells in the microplate and dispense direction set in advance. Therefore, the present invention provides an operationally superior control device for the automatic liquid handling system, that makes it unnecessary for the operator to determine in advance the arrangement of dispensing tips and other time-consuming tasks.

The control device can also calculate the quantity of reagent to be used and the arrangement of reagent using information on specific reagent, the quantity of reagent to be dispensed into one well, the range of wells in the microplate into which reagent is to be dispensed, and the dispense direction set in advance. Therefore, the present invention can provide an automatic liquid handling system that is superior regarding ease of use.

What is claimed is:

1. An automatic liquid handling system comprising:
    a first dispensing tip container;
    a second dispensing tip container, each of the first and second dispensing tip containers having a plurality of holding portions for holding dispensing tips, each of the holding portions being arranged in a matrix form defined by rows and columns;
    a dispensing head having attachment portions to which the dispensing tips are attached, wherein when the dispensing tips are attached to the attachment portions, the dispensing head is capable of performing sucking and expelling operations for sucking liquid in or expelling the liquid out from the dispensing tips;
    a moving mechanism that moves the dispensing head;
    a first reagent container;

a second reagent container, each of the first and second reagent containers having a plurality of container portions arranged side-by-side, wherein the plurality of container portions of the first reagent container extend in a direction of rows and the plurality of container portions of the second reagent container extend in a direction of columns;

a microplate formed with a plurality of wells for holding specimen, the wells being arranged in a matrix form defined by rows and columns;

a control device that controls the sucking and expelling operations performed by the dispensing head and also controls the moving mechanism to control movements of the dispensing head, wherein the control device includes an input portion for inputting a process to be executed, the process including at least one of information regarding reagent to be used, information of a dispense volume per well of the microplate, information of the number of wells in which the reagent is to be dispensed and information regarding dispensing direction, a first determining unit that determines an arrangement of dispensing tips to be set at the holding portions of the first and second dispensing tip containers based on the input information, and second determining unit that determines an arrangement of reagent to be stored at the container portions of the first and second reagent containers based on the input information; and a display that indicates the arrangement of the dispensing tips to be set at the holding portions and the arrangement of the reagent to be stored at the reagent container portions.

2. The automatic liquid handling system according to claim 1, wherein the control device further includes a simulating portion that simulates an operation time to execute the inputted process and determines whether the process can be completed within a predetermined period of time.

3. An automatic liquid handling system comprising:

a first dispensing tip container having a plurality of holding portions for holding dispensing tips, the holding portions being arranged in a matrix form defined by rows and columns;

a dispensing head having attachment portions to which at least one dispensing tip is attached, wherein when one or more dispensing tips are attachable to the attachment portions, the dispensing head is configured to perform sucking and expelling operations for sucking liquid in or expelling the liquid out from the one or more dispensing tips;

a moving mechanism that moves the dispensing head;

a first reagent container storing a reagent;

a microplate formed with a plurality of wells for holding specimen, the wells being arranged in a matrix form defined by rows and columns;

a control device that controls the sucking and expelling operations performed by the dispensing head and also controls the moving mechanism to control movements of the dispensing head, wherein the control device includes an input portion for inputting one or more processes to be executed by the dispensing head, the process including information regarding a dispensing direction on the matrix form to dispense the reagent into the wells of the microplate, and information regarding a range of the wells on each of the rows or each of the columns into which the reagent is dispensed, and a determining section that determines an arrangement of dispensing tips to be set at the holding portions of the first dispensing container based on the inputted information; and a display for indicating the arrangement of the dispensing tips determined by the determining section.

4. The automatic liquid handling system according to claim 3, wherein the display indicates the arrangement of the dispensing tips using different colors for each of the processes.

5. The automatic liquid handling system according to claim 3, wherein the control device includes a storage section that stores information regarding the arrangement of the dispensing tips determined by the determining section.

6. The automatic liquid handling system according to claim 3, wherein the moving mechanism moves the dispensing head in a three dimensional space defined by X-axis, Y-axis, and Z-axis, the moving mechanism further swiveling the dispensing head in a plane defined by the X-axis and the Y-axis wherein the X-axis is oriented in a direction of the rows and the Y-axis is oriented in a direction of the columns.

7. The automatic liquid handling system according to claim 3, further comprising a second reagent container storing a reagent, each of the first and second reagent containers having a plurality of container portions arranged side-by-side, plural kinds of reagents being stored separately in the plurality of container portions.

8. The automatic liquid handling system according to claim 7, wherein the plurality of container portions of the first regent container extends in a direction of the rows and the plurality of container portions of the second reagent container extends in a direction of columns.

9. The automatic liquid handling system according to claim 7, wherein the control device further includes a second determining section that determines an arrangement of the reagent to be stored at the container portions of the first and the second reagent containers based on the inputted information.

10. The automatic liquid handling system according to claim 3, further comprising a second dispensing tip container having a plurality of holding portions for holding dispensing tips, the holding portions of the second dispensing tip container being arranged in a matrix form defined by rows and columns.

11. The automated liquid handling system according to claim 3, wherein the control device further includes a calculating section that calculates a volume of the reagent to be dispensed into the wells of the microplate based on the inputted information.

12. An automatic liquid handling system comprising:

a first dispensing tip container having a plurality of holding portions for holding dispensing tips, the holding portions being arranged in a matrix form defined by rows and columns;

a dispensing head having attachment portions to which at least one dispensing tip is attachable, wherein when one or more dispensing tips are attached to the attachment portions, the dispensing head is capable of performing sucking and expelling operations for sucking liquid in or expelling the liquid out from the one or more dispensing tips;

a moving mechanism that moves the dispensing head;

a first reagent container;

a second reagent container, each of the first and second reagent containers having a plurality of container portions arranged side-by-side wherein the plurality of container portions of the first reagent container extends in a direction of rows and the plurality of container portions of the second reagent container extends in a direction of columns;

a microplate formed with a plurality of wells for holding specimen, the walls being arranged in a matrix form defined by rows and columns;

a control device that controls the sucking and expelling operations performed by the dispensing head and also controls the moving mechanism to control movements of the dispensing head, wherein the control device includes an input portion for inputting one or more processes to be executed by the dispensing head, the process including information regarding a dispensing direction on the matrix form to dispense the reagent into the wells of the microplate, and information regarding a range of the wells on each of the rows or each of the columns into which the reagent is dispensed, a determining section that determines an arrangement of the reagent to be stored at the container portions of the first and the second reagent containers based on the input information; and a display for indicating the arrangement of the reagent to be stored at the container portions.

13. The automatic liquid handling system according to claim 12, wherein the display indicates the arrangement of the reagent using different colors for each of the processes.

14. The automatic liquid handling system according to claim 12, wherein the moving mechanism moves the dispensing head in a three dimensional space defined by X-axis, Y-axis, and Z-axis, the moving mechanism further swiveling the dispensing head in a plane defined by the X-axis and the Y-axis wherein the X-axis is oriented in a direction of the rows and the Y-axis is oriented in a direction of the columns.

15. The automatic liquid handling system according to claim 12, further comprising a second dispensing tip container having a plurality of holding portions for holding dispensing tips, the holding portions of the second dispensing tip container being arranged in a matrix form defined by rows and columns.

16. The automatic liquid handling system according to claim 12, wherein the control device further includes a calculating section that calculates a volume of the reagent to be dispensed into the wells of the microplate based on the inputted information.

17. The automatic liquid handling system according to claim 12, wherein the control device includes a storage section that stores information regarding the arrangement of the reagent to be stored in the reagent container.

18. A method for operating an automatic liquid handling system including a dispensing tip container having a plurality of holding portions for holding dispensing tips, a dispensing head having attachment portions to which at least one dispensing tip is attached, a moving mechanism that moves the dispensing head, a reagent container that holds reagent, a microplate formed with a plurality of wells for holding specimen, and a control device that controls sucking and expelling operations performed by the dispensing head and also controls the moving mechanism to control movements of the dispensing head, the control device having an input portion for inputting one or more processes to be executed by the dispensing head, wherein the method comprises:

a first step of inputting information into the control device by using the input portion, the information including process to be executed, reagent to be used, dispense quantity, a range of dispensing wells in the microplate and a predetermined period of time set to execute the process;

a second step of determining arrangement of dispensing tips to be set in the dispensing tip containers based on the input information regarding the dispensing wells in the microplate;

a third step of determining arrangement of reagent to be stored in the reagent containers based on the input information regarding the reagent to be used and dispense quantity; and a fourth step of simulating the operation time to execute the inputted process and determining whether the process can be completed within the predetermined period of time so as to inform an operator of a result of the determining.

* * * * *